United States Patent
Lee et al.

(10) Patent No.: US 11,391,684 B2
(45) Date of Patent: Jul. 19, 2022

(54) METHOD FOR MEASURING AROMATIC CONTENTS IN HYDROCARBON SOLUTION

(71) Applicant: Hanwha Solutions Corporation, Seoul (KR)

(72) Inventors: Yong Hee Lee, Anyang-si (KR); Wan Jae Myeong, Daejeon (KR); Woo Jin Park, Seongnam-si (KR); Bong Sik Jeon, Daejeon (KR); Eui Geun Jung, Seoul (KR)

(73) Assignee: HANWHA SOLUTIONS CORPORATION, Seoul (KR)

(*) Notice: Subject to any disclaimer, the term of this patent is extended or adjusted under 35 U.S.C. 154(b) by 227 days.

(21) Appl. No.: 16/769,690

(22) PCT Filed: Nov. 29, 2018

(86) PCT No.: PCT/KR2018/014972
§ 371 (c)(1),
(2) Date: Jun. 4, 2020

(87) PCT Pub. No.: WO2019/132269
PCT Pub. Date: Jul. 4, 2019

(65) Prior Publication Data
US 2020/0371053 A1 Nov. 26, 2020

(30) Foreign Application Priority Data
Dec. 27, 2017 (KR) .................. 10-2017-0181544

(51) Int. Cl.
*G01N 25/12* (2006.01)
*G01N 24/08* (2006.01)

(52) U.S. Cl.
CPC ............ *G01N 25/12* (2013.01); *G01N 24/08* (2013.01)

(58) Field of Classification Search
CPC .... G01N 25/12; G01N 24/08; G01N 33/2823; G01N 33/2811; G01N 24/082
See application file for complete search history.

(56) References Cited

U.S. PATENT DOCUMENTS

| 7,510,674 B2 | 3/2009 | Rosenbaum et al. |
| 7,981,270 B2 | 7/2011 | Rosenbaum et al. |

(Continued)

FOREIGN PATENT DOCUMENTS

| JP | 62-035621 | 7/1981 |
| JP | 4-227675 | 8/1992 |

(Continued)

OTHER PUBLICATIONS

Masakichi Mizuda, general properties of crude oil gasoline oil from Japan and the composition of hydrocarbons (Article 4) A Study on the General Quantification of Aromatic Hydrocarbons, Nippon Oil Co., Ltd., vol. 9 No. 34, Jul. 23, 1931 & its English Translations of relevant pages.

(Continued)

*Primary Examiner* — G.M. A Hyder
(74) *Attorney, Agent, or Firm* — Lex IP Meister, PLLC

(57) ABSTRACT

The present disclosure relates to a method for measuring aromatic contents in a hydrocarbon solution. More specifically, it relates to a measurement method capable of quickly and accurately checking aromatic contents in a compound, particularly in a hydrocarbon, in a solution state without a high-temperature drying process.

8 Claims, 1 Drawing Sheet

(56) References Cited

U.S. PATENT DOCUMENTS

| | | | |
|---|---|---|---|
| 2015/0106027 A1 | 4/2015 | Koseoglu et al. | |
| 2015/0106029 A1* | 4/2015 | Koseoglu | G01N 30/88 702/23 |
| 2015/0106032 A1 | 4/2015 | Koseoglu et al. | |

FOREIGN PATENT DOCUMENTS

| | | |
|---|---|---|
| JP | 6-88819 | 3/1994 |
| JP | 07-138350 | 5/1995 |
| JP | 2004-184082 | 7/2004 |
| JP | 2008-522384 | 6/2008 |
| JP | 2008-533247 | 8/2008 |
| JP | 2009-098116 | 5/2009 |
| KR | 10-2017-0121166 | 11/2017 |
| WO | 2015-147027 | 10/2015 |
| WO | 2016-111989 | 7/2016 |

OTHER PUBLICATIONS

KIPO, PCT Search Report & Written Opinion of PCT/KR2018/014972 dated Mar. 6, 2019.
Emmett P. O'Brien et al., "Fundamentals of hot-melt pressure-sensitive adhesive tapes: the effect of tackifier aromaticity", PJournal of adhesion science and technology vol. 21, No. 7, Jan. 1, 2007, pp. 637-661.
EPO, Extended European Search Report of EP 18896720.2 dated Aug. 2, 2021.

* cited by examiner

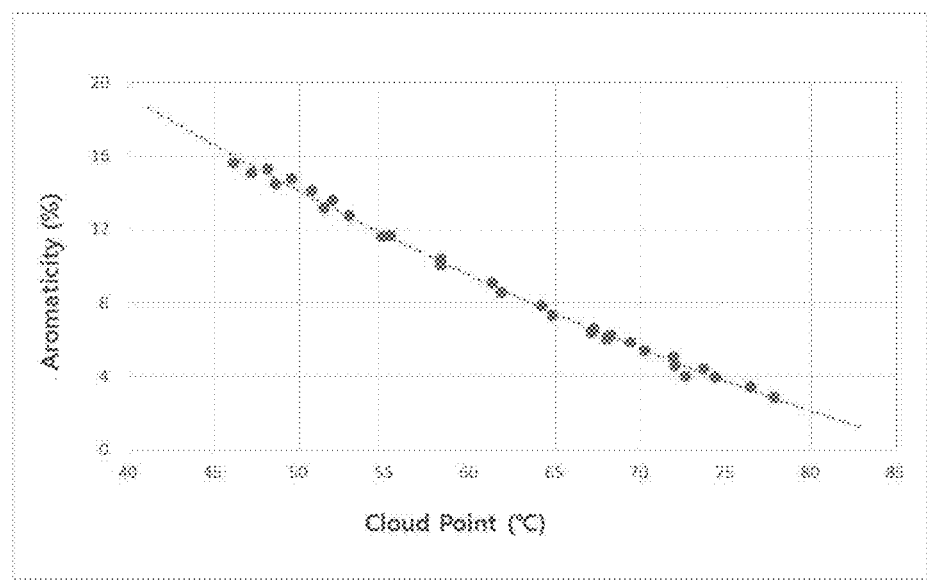

METHOD FOR MEASURING AROMATIC CONTENTS IN HYDROCARBON SOLUTION

BACKGROUND OF THE INVENTION

(a) Field of the Invention

CROSS-REFERENCE TO RELATED APPLICATION(S)

This application claims the benefit of Korean Patent Application No. 10-2017-01 81 544 filed on Dec. 27, 2017 with the Korean Intellectual Property Office, the disclosures of which are incorporated herein by reference in their entirety.

The present disclosure relates to a method for measuring aromatic contents in a hydrocarbon solution. More specifically, it relates to a measurement method capable of quickly and accurately checking aromatic contents in a compound, particularly in a hydrocarbon, in a solution state without a high-temperature drying process.

(b) Description of the Related Art

In general, a hydrogenation process for a hydrocarbon compound is a reaction applied to reduce a specific functional group or convert an unsaturated compound into a saturated compound. In the hydrogenation process, which is one of the commercially important reactions, a compound having an unsaturated functional group such as ketone, aldehyde, imine, or the like is reduced to a compound such as alcohol, amine, or the like, or an unsaturated bond of an olefin compound or an aromatic compound is saturated.

In the hydrogenation process, it is necessary to selectively hydrogenate any one of aromatic and olefin bonds depending on the application. Since the aromatic contents in the reaction product are one of main factors determining a quality of the hydrogenated resin in the selective hydrogenation reaction, it is important to measure the aromatic contents of the product after the hydrogenation reaction. Herein, the aromatic contents are defined as an amount of hydrogen contained in the aromatic group of all hydrogen in the compound. To measure the aromatic contents, H-NMR analysis or mixed methylcyclohexane-aniline point (MMAP) analysis is mainly used.

In order to monitor the aromatic contents during the operation of the reaction process, it is necessary to analyze the aromatic contents of the solution under reaction in a short time. However, all of the above methods have a disadvantage in that a process of drying a solvent of the hydrogenation product at a high temperature is essential, which takes a long time. In addition, when H-NMR is used, an expensive NMR instrument is required, which results in high analytical costs.

SUMMARY OF THE INVENTION

The present disclosure is intended to solve the problems of the prior art described above. In the present disclosure, there is provided a method for measuring aromatic contents in a hydrocarbon solution, which does not require a high-temperature drying process of a solvent, shortens the time required for measurement, has low analytical costs, and has high accuracy.

According to an embodiment of the present disclosure, there is provided a method for measuring aromatic contents, including the steps of:

mixing a hydrocarbon solution and aniline at room temperature in a volume ratio of 1:1;

heating the mixed solution of the hydrocarbon solution and aniline until it becomes transparent;

measuring a cloud point while cooling the transparent mixed solution; and calculating aromatic contents in the hydrocarbon solution by substituting the cloud point into a calibration curve.

According to the method of the present disclosure, it is possible to check aromatic contents of a hydrocarbon compound in a solution state without a high-temperature drying process. Since the high-temperature drying process is unnecessary, the time required for analysis can be significantly shortened compared to the conventional method.

In addition, since an expensive and large-scale instrument such as NMR is not required and reagents other than aniline are unnecessary, analytical costs are very low compared to the conventional method.

In addition, the method uses only aniline as a reagent and the measurement is relatively simple, so measurement errors are small and accuracy is high. Therefore, it is expected to be useful in production.

BRIEF DESCRIPTION OF THE DRAWINGS

FIG. 1 is a calibration curve with a cloud point of a hydrocarbon solution as an x-axis and aromatic contents of the same as a y-axis.

DETAILED DESCRIPTION OF THE EMBODIMENTS

As the present invention can be variously modified and have various forms, specific embodiments thereof are shown by way of examples and will be described in detail. However, it is not intended to limit the present invention to the particular form disclosed and it should be understood that the present invention includes all modifications, equivalents, and replacements within the idea and technical scope of the present invention.

The terminology used herein is for the purpose of describing particular embodiments only and is not intended to be limiting of the invention. The singular forms are intended to include the plural forms as well, unless the context clearly indicates otherwise. It will be further understood that the terms "include", "have", or "possess" when used in this specification, specify the presence of stated features, steps, components, or combinations thereof, but do not preclude the presence or addition of one or more other features, steps, components, or combinations thereof.

Also, as used herein, in case an element is mentioned to be formed "on" elements, it means that the element is directly formed on the elements, or it means that other elements may be additionally formed between layers, on a subject, or on a substrate.

Hereinafter, the method for measuring aromatic contents in a hydrocarbon solution of the present disclosure will be described in more detail.

The method for measuring aromatic contents according to an embodiment of the present disclosure includes the steps of: mixing a hydrocarbon solution and aniline at room temperature in a volume ratio of 1:1; heating the mixed solution of the hydrocarbon solution and aniline until it becomes transparent; measuring a cloud point while cooling the transparent mixed solution; and calculating aromatic contents in the hydrocarbon solution by substituting the cloud point into a calibration curve.

It is necessary to measure aromatic contents in a particular compound or solution for various purposes. For example, there may be a case in which a selective hydrogenation reaction selectively hydrogenating any one unsaturated bond is performed for a compound containing both an aromatic bond and an olefin bond, and then a hydrogenation selectivity of the product according to the selective hydrogenation reaction is determined. In particular, in the case of the selective hydrogenation reaction for a petroleum resin, since physical properties and uses of the hydrogenated petroleum resin can vary greatly depending on the selectivity, it is necessary to more accurately and quickly measure the aromatic contents.

In the present disclosure, the aromatic contents may be defined as an amount (%) of hydrogen contained in the aromatic group of all hydrogen in the compound.

For this purpose, the most widely used method for measuring the aromatic contents in a compound is H-NMR analysis or mixed methylcyclohexane-aniline point (MMAP) analysis.

The H-NMR analysis is performed by removing a solvent from a solution containing a compound to be measured, recovering the compound from which the solvent has been removed and then analyzing it with an NMR instrument, and has high accuracy.

The MMAP analysis is performed by removing a solvent from a solution containing a compound to be measured, dissolving the compound from which the solvent has been removed in a solvent in which methylcyclohexane and aniline are mixed in a ratio of 1:2, and then measuring a cloud point of the mixed solution.

As described above, both the H-NMR analysis and the MMAP analysis require a process of removing the solvent before measurement, and there is a problem that the removal of the solvent is performed by a high-temperature drying, which takes a lot of time. In addition, an expensive large-scale instrument is required for the NMR analysis, which results in high analytical costs. In the MMAP analysis, the use of several solvents leads to an increase in analytical costs, and measurement errors frequently occur because two or more solvents must be mixed in a predetermined ratio.

The present disclosure is to improve the problems of the conventional method, and provides a very effective measurement method which does not require a drying process of a solvent and uses only aniline as a reagent. Thus, the method is simple and inexpensive, and has little measurement error.

The present inventors have completed the present invention by focusing on the fact that a cloud point of a mixed solution of a hydrocarbon compound containing an aromatic bond and aniline is proportional to aromatic contents in the compound.

That is, a mixed solution of a specific compound in which aromatic contents are known in advance and aniline is prepared, and its cloud point is measured to obtain a calibration curve indicating a relationship between the aromatic contents in the compound solution and the cloud point. Therefore, it is possible to quickly and accurately measure aromatic contents in a sample solution by mixing an unknown sample solution with unknown aromatic contents with aniline, measuring a cloud point of the mixed solution, and substituting the measured cloud point into the calibration curve.

In the method for measuring aromatic contents of the present disclosure, a hydrocarbon solution and aniline are first mixed.

In the method for measuring aromatic contents of the present disclosure, the hydrocarbon compound to be measured may be any compound containing an aromatic bond, and is not particularly limited. Also, a single compound or a mixture of two or more compounds may be subject to measurement.

According to an embodiment of the present disclosure, the hydrocarbon compound may be a petroleum resin obtained after a hydrogenation reaction, but the present disclosure is not limited thereto.

As described above, the hydrocarbon compound may be used for measurement as it is in a solution state dissolved in a solvent, and does not require a solvent removal process. Further, the solvent is not particularly limited as long as it is an organic solvent that can dissolve the hydrocarbon compound and does not contain an aromatic component, and examples thereof include cyclohexane, n-nonane, and n-decane.

In addition, a concentration of the solution does not matter, but the solution may have an appropriate viscosity for convenience of measurement. For example, the solution may contain the hydrocarbon compound to be measured in 10 to 90 wt %.

The hydrocarbon solution and aniline are mixed at room temperature in a volume ratio of 1:1 to prepare a mixed solution.

The mixing method is not particularly limited, and any method such as a method in which the hydrocarbon solution is first introduced in a container and aniline is introduced, a method in which aniline is first introduced in a container and the hydrocarbon solution is introduced, or a method in which the hydrocarbon solution and aniline are simultaneously introduced may be used.

Next, the mixed solution is gradually heated until it becomes transparent. In the mixed solution, the hydrocarbon solution and aniline are not mixed with each other at room temperature, and are in a layered state. As the temperature rises, they are mixed and eventually become transparent. At this time, the temperature at which the mixed solution becomes transparent varies depending on the aromatic contents in the hydrocarbon.

The heating step may be performed by placing a container containing the mixed solution on a heating means such as a heating plate, and then heating, but the present disclosure is not limited thereto.

In addition, a heating rate is not particularly limited, but the temperature may be increased at a rate of, for example, 1 to 10° C./min to prevent a sudden increase in temperature.

According to an embodiment of the present disclosure, it may be desirable to heat the mixed solution with stirring at a constant rate using a magnetic bar, or the like to minimize a difference in temperature between the upper and lower parts of the mixed solution.

Next, a cloud point is measured while cooling the transparent mixed solution.

When the mixed solution is gradually cooled while stirring, aniline and the hydrocarbon solution start to separate again from the upper part of the mixed solution, and a cloud state in which a part is blurred is formed. A temperature at which the hydrocarbon solution and aniline are completely separated, and the entire mixed solution becomes cloudy is measured as a cloud point.

At this time, according to an embodiment of the present disclosure, it is preferable to set the cooling rate to 2° C./min or less, for example, 0.5 to 2° C./min, to minimize an observation error of the cloud point, and the cooling may also be performed with stirring.

In addition, the cooling may be performed by a method in which the container containing the mixed solution is taken out of the heating means and left at room temperature, a method of cooling as it is on the heating means to control the cooling rate, or a method of cooling in a water bath, but the present disclosure is not limited thereto.

The aromatic contents in the hydrocarbon compound are calculated by substituting the cloud point measured in this way into a calibration curve.

The calibration curve is a graph indicating a relationship between the aromatic contents and the cloud point in the hydrocarbon compound solution obtained by measuring the aromatic contents of the same compound as the hydrocarbon compound to be measured in advance by another method (e.g., H-NMR analysis), and measuring the cloud point as described above.

The aromatic contents measured by the method of the present disclosure may have high accuracy with a measurement error within ±5% compared to the aromatic contents measured by H-NMR analysis.

Hereinafter, the present invention will be described in more detail through Examples and Comparative Examples, but this is for the purpose of helping specific understanding of the invention and the scope of the present invention is not limited by Examples or Comparative Examples.

EXAMPLES

Preparation Example: Analysis of Relationship Between Cloud Point and Aromatic Contents A cloud point of a hydrocarbon solution having aromatic contents of 1% to 20% was measured in the following manner. At this time, the aromatic contents of the sample were previously measured by standardized H-NMR.

First, 10 mL of aniline was mixed with 10 mL of a petroleum resin sample solution in which a petroleum resin was dissolved in an Exxsol D40 solvent at 60 wt % in a 30 mL vial to prepare a compound to be measured. Thereafter, the vial containing the mixed solution of the sample solution and aniline was heated to 90° C. using a heating plate while stirring at 400 rpm using a magnetic bar, and it was confirmed that the mixed solution was completely transparent.

While cooling the mixed solution at a rate of 2° C./min with stirring, the temperature at which the entire mixed solution became cloudy was measured as a cloud point.

A graph with a cloud point of the mixed solution as an x-axis and aromatic contents measured by H-NMR analysis as a y-axis was shown in FIG. 1, and referred to as a calibration curve.

Example 1

10 mL of aniline was mixed with 10 mL of a petroleum resin sample solution in which a petroleum resin was dissolved in an Exxsol D40 solvent at 60 wt %, which is predicted to have aromatic contents of 5% or less, in a 30 mL vial. Thereafter, the vial containing the mixed solution of the sample solution and aniline was heated to 90° C. using a heating plate while stirring at 400 rpm using a magnetic bar, and it was confirmed that the mixed solution was completely transparent.

While cooling the mixed solution at a rate of 2° C./min with stirring, the temperature at which the entire mixed solution became cloudy was measured as a cloud point. At this time, aromatic contents were measured by substituting the cloud point into the calibration curve of FIG. 1.

In addition, aromatic contents of the petroleum resin obtained after heating the sample solution at 200° C. to remove the solvent were measured by H-NMR analysis, and the results were compared.

Example 2

A cloud point was measured in the same manner as in Example 1 using a petroleum resin sample solution in which a petroleum resin was dissolved in an Exxsol D40 solvent at 60 wt %, which is predicted to have aromatic contents of 5% to 10%, and aromatic contents were measured by substituting the cloud point into the calibration curve of FIG. 1.

In addition, aromatic contents of the petroleum resin obtained after heating the sample solution at 200° C. to remove the solvent were measured by H-NMR analysis, and the results were compared.

Example 3

A cloud point was measured in the same manner as in Example 1 using a petroleum resin sample solution in which a petroleum resin was dissolved in an Exxsol D40 solvent at 60 wt %, which is predicted to have aromatic contents of 10% or more, and aromatic contents were measured by substituting the cloud point into the calibration curve of FIG. 1.

In addition, aromatic contents of the petroleum resin obtained after heating the sample solution at 200° C. to remove the solvent were measured by H-NMR analysis, and the results were compared.

For Examples 1 to 3, the aromatic contents measured by the method of the present disclosure and the aromatic contents measured by NMR are shown in Table 1 below.

TABLE 1

| | Cloud point method | | Aromatic contents |
|---|---|---|---|
| | Cloud point (° C.) | Aromatic contents (%) | measured by H-NMR (%) |
| Example 1 | 75.4 | 3.6 | 3.6 |
| Example 2 | 65.0 | 7.4 | 7.6 |
| Example 3 | 57.6 | 10.5 | 10.8 |

Referring to Table 1 above, it was confirmed that the aromatic contents measured according to the method of the present disclosure had very high accuracy with an error of 5% or less, compared to the aromatic contents measured by NMR.

What is claimed is:

1. A method for measuring aromatic contents, comprising the steps of:
   mixing a hydrocarbon solution and aniline at room temperature in a volume ratio of 1:1;
   heating the mixed solution of the hydrocarbon solution and aniline until it becomes transparent;
   measuring a cloud point while cooling the transparent mixed solution; and
   calculating aromatic contents in the hydrocarbon solution by substituting the cloud point into a calibration curve.

2. The method for measuring aromatic contents of claim 1,
   wherein the hydrocarbon solution contains 10 to 90 wt % of hydrocarbon.

3. The method for measuring aromatic contents of claim 1,
   wherein the steps of heating and cooling the mixed solution are performed while stirring the mixed solution.

4. The method for measuring aromatic contents of claim 1,
   wherein the step of cooling the transparent mixed solution is performed at a cooling rate of 2° C./min or less.

5. The method for measuring aromatic contents of claim 1,
   wherein the calibration curve is a graph indicating a relationship between the aromatic contents and the cloud point in the hydrocarbon to be measured obtained by measuring the aromatic contents of the same compound as the hydrocarbon to be measured in advance by H-NMR analysis.

6. The method for measuring aromatic contents of claim 1,
   wherein the hydrocarbon solution is obtained after a hydrogenation reaction.

7. The method for measuring aromatic contents of claim 1,
   wherein the hydrocarbon is a petroleum resin.

8. The method for measuring aromatic contents of claim 1,
   wherein a solvent of the hydrocarbon solution is an organic solvent containing no aromatics.

* * * * *